US006951831B2

(12) United States Patent
Lecocq et al.

(10) Patent No.: US 6,951,831 B2
(45) Date of Patent: Oct. 4, 2005

(54) CATALYST COMPOSITION FOR DIMERIZING, CO-DIMERIZING, OLIGOMERIZING AND POLYMERIZING OLEFINS

(75) Inventors: Vincent Lecocq, Paris (FR); Hélène Olivier-Bourbigou, Rueil Malmaison (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 193 days.

(21) Appl. No.: 10/356,745

(22) Filed: Feb. 3, 2003

(65) Prior Publication Data

US 2003/0220191 A1 Nov. 27, 2003

(30) Foreign Application Priority Data

Feb. 4, 2002 (FR) ............................................ 02 01252
Feb. 4, 2002 (FR) ............................................ 02 01250

(51) Int. Cl.$^7$ ............................ B01J 71/00; C07C 2/02; C07C 2/24; C08F 4/44; C08F 4/80

(52) U.S. Cl. ....................... 502/162; 502/164; 502/167; 502/168; 585/512; 585/513; 585/525; 585/526; 585/527; 585/531; 526/134; 526/139; 526/140; 526/141; 526/145; 526/146; 526/147; 526/171; 526/172

(58) Field of Search ................................. 502/162, 164, 502/167, 168; 585/512, 513, 527, 531, 525, 526; 526/171, 172, 134, 139–141, 145–147

(56) References Cited

U.S. PATENT DOCUMENTS 5,104,840 A  *  4/1992  Chauvin et al. ............. 502/117
5,744,678 A  *  4/1998  Aida et al. .................. 585/513
6,576,724 B2 *  6/2003  Olivier-Bourbigou et al. ... 526/139
6,667,269 B2 * 12/2003  Olivier-Bourbigou et al. ... 502/117
6,706,657 B2 *  3/2004  Commereuc et al. ....... 502/164

FOREIGN PATENT DOCUMENTS

DE      19901524      7/2000
FR       2611700      9/1988

OTHER PUBLICATIONS

Journal of Fluorine Chemistry 105 (2000) 221–227, Room temperature ionic liquids of alkylimidazolium cations and fluoroanlons, Rika Haglwara et al., Department of Fundamental Energy Science, Kyoto University, Sakyo–ku, Kyoto 606–8501, Japan.
Macromol. Rapid Commun. 2001, 22, 425–428, Biphasic Ethylene Polymerization with a Diminenickel Catalyst, XP–001038811, Mauricio F. Pinhelro et al., Instituto de Quimica, Universidade Federal do Rio Grande do Sul, P.O. Box 15003, CEP 91501–970, Porto Alegre, Brazil.
Organometatics 1999, 18, 65–74, XP–000926108, Ethylene Oligomerization and Propylene Dimerization Using Cationic (α–Dilmine)nickel(II) Catalysts, Steven A. Svejda et al, Department of Chemistry, University of North Carolina at Chapel Hill, Chapel Hill, North Carolina 27599–3290.

* cited by examiner

Primary Examiner—J.A. Lorengo
Assistant Examiner—J. Pasterczyk
(74) Attorney, Agent, or Firm—Millen, White, Zelano & Branigan, P.C.

(57) ABSTRACT

A catalyst composition for use in dimerizing, co-dimerizing or oligomerizing olefins comprises:
  at least one zero-valent nickel complex;
  at least one acid with formula $H^+X^-$ in which $X^-$ represents an anion;
  and at least one ionic liquid with general formula $Q^+A^-$ in which $A^-$ is an anion identical to or different from $X^-$.

The composition can also comprise a nitrogen-containing ligand. It can be used in dimerizing, co-dimerizing, oligomerizing and in polymerizing olefins.

24 Claims, No Drawings

CATALYST COMPOSITION FOR DIMERIZING, CO-DIMERIZING, OLIGOMERIZING AND POLYMERIZING OLEFINS

BACKGROUND OF THE INVENTION

1. Field of the Invention

The present invention relates to dimerizing, co-dimerizing or oligomerizing and also polymerizing olefins. More particularly, it relates to a catalyst composition for catalyzing the reactions occurring in those processes.

α-linear olefins, in particular those containing 4 to 10 carbon atoms, used as co-monomers for producing low density polyethylene (LLDPE) or as intermediates in producing detergents or lubricants, are becoming more important commercially. The majority of industrial processes for producing α-olefins are processes for oligomerizing ethylene catalyzed by transition metal complexes (Ni, Ti, Zr) or AlEt$_3$ (Alpha Olefins Applications Handbook, G. R. Lapin and J. D. Sauer, Eds, M. Dekker, N.Y., 1989). The majority of those processes result in broad distributions of α-olefins: $C_4$ to $C_{20}^+$.

2. Description of the Prior Art

We are constantly researching novel catalytic systems that can produce narrower olefin distributions, for example to optimize the formation of $C_4$–$C_{10}$, and which are more selective for linear α-olefins and more active.

It has recently been demonstrated (S Svejda et al, Organometallics, 1999, 18, 65–74; International Patent applications WO 96/02310; WO 00/10945; U.S. Pat. No. 5,880,323) that systems comprising a nickel complex in combination with nitrogen-containing ligands of the α-type diimine in the presence of a Lewis acid or a Brønsted acid, and more particularly an aluminum derivative such as an aluminoxane or an alkyl aluminum chloride, can catalyze the oligomerization of ethylene to linear α-olefins. However, in such systems, large quantities of aluminoxane are generally used (more than 100 equivalents per mole of nickel) and the distribution of the olefins formed is generally wide: $C_4$ to $C_{20}$, with a Schulz-Flory constant of more than 0.6.

Further, neutral nickel complexes comprising chelated P—O type ligands have been used for more than 20 years as precursors in the "SHOP" process from Shell for the oligomerization of ethylene to $C_4$–$C_{20}^+$ linear α-olefins. The particular feature of that process is that the nickel complex is dissolved in a polar diol type solvent such as 1,4-butanediol, in which the reaction products are only slightly miscible. This two-phase operation enables the products to be separated by decanting and allows the catalyst to be recycled.

French Patent No. 2,611,700 describes the use of liquids with an ionic nature formed from aluminum halides and quaternary ammonium halides as solvents for organometallic nickel complexes for catalyzing olefin dimerization. The use of such media which are not miscible with aliphatic hydrocarbons, in particular with olefin dimerization products, allows better use of homogeneous catalysts. Further, such media can be used with organometallic complexes, which are reactive in the presence of protic compounds such as the diols described in the "SHOP" process.

U.S. Pat. No. 5,104,840 describes a liquid composition with an ionic nature resulting from contacting quaternary ammonium halides and/or quaternary phosphonium halides with alkyl aluminum dihalides and an optional aluminum trihalide. That patent also describes the use of such media as solvents for transition metal complexes, in particular nickel complexes containing no nickel-carbon bond, which are transformed into catalysts for oligomerizing olefins.

SUMMARY OF THE INVENTION

We have now discovered a novel catalyst composition in the form of a solution that comprises at least one zero-valent nickel complex; at least one acid with formula $H^+ X^-$ in which $X^-$ represents an anion; and at least one ionic liquid with general formula $Q^+A^-$ in which $Q^+$ represents a quaternary ammonium cation and/or a quaternary phosphonium cation and/or a sulfonium cation and in which $A^-$ is an anion identical to or different from $X^+$ and represents any anion that is capable of forming a liquid salt with $Q^+$ at low temperature, i.e., below 150° C.

This novel catalyst composition is capable of dimerizing, co-dimerizing and oligomerizing olefins.

DETAILED DESCRIPTION OF THE INVENTION

The nickel compounds used in accordance with the invention are complexes of zero-valent nickel. Non limiting examples that can be cited are nickel bis(cycloocta-1,3-diene), nickel bis(cyclooctatetraene), nickel bis(cycloocta-1,3,7-triene), bis(o-tolylphosphito)nickel(ethylene), nickel tetrakis(triphenylphosphite) and nickel bis(ethylene).

In the non aqueous ionic liquid with general formula $Q^+A^-$, anion $A^-$ is preferably selected from nitrate, sulfate, phosphate, acetate, halogenoacetate, tetrafluoroborate, tetrachloroborate, hexafluorophosphate, hexafluoroantimonate, fluorosulfonate, alkylsulfonates (for example methylsulfonate), perfluoroalkylsulfonates (for example trifluoromethylsulfonate), bis(perfluoroalkylsulfonyl) amides (for example bis-trifluoromethanesulfonyl amide with formula $N(CF_3SO_2)_2^-$), tris-trifluoromethanesulfonyl methylide with formula $C(CF_3SO_2)_3^-$, arenesulfonates, optionally substituted with halogen or halogenalkyl groups, carborane anions, and the tetraphenylborate anion along with tetraphenylborate anions the aromatic rings of which have been substituted.

The quaternary ammonium and/or phosphonium cations preferably have general formulae $NR^1R^2R^3R^{4+}$ and $PR^1R^2R^3R^{4+}$, or general formulae $R^1R^2N=CR^3R^{4+}$ and $R^1R^2P=CR^3R^{4+}$ in which $R^1$, $R^2$, $R^3$ and $R^4$, which may be identical or different, each represent a hydrogen atom (with the exception of the cation $NH_4^+$ for $NR^1R^2R^3R^{4+}$); preferably a single substituent represents hydrogen, or hydrocarbyl residues containing 1 to 30 carbon atoms, for example alkyl groups, saturated or unsaturated groups, cycloalkyl or aromatic, aryl or aralkyl groups, which may be substituted, containing 1 to 30 carbon atoms.

The ammonium and/or phosphonium cations can also be derived from nitrogen-containing and/or phosphorus-containing heterocycles containing 1, 2 or 3 nitrogen and/or phosphorus atoms, with general formulae:

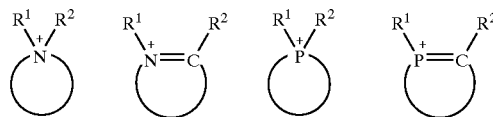

in which the cycles are constituted by 4 to 10 atoms, preferably 5 or 6 atoms, and $R^1$ and $R^2$ are as defined above.

The quaternary ammonium or phosphonium cation can also have one of the following general formulae:

in which $R^1$, $R^2$ and $R^3$, which may be identical or different, are defined as above and $R^5$ represents an alkylene or phenylene residue. Groups $R^1$, $R^2$, $R^3$, $R^4$ that can be mentioned include the methyl, ethyl, propyl, isopropyl, secondary butyl, tertiary butyl, butyl, amyl, phenyl and benzyl radicals; $R^5$ can be a methylene, ethylene, propylene or phenylene group.

The ammonium and/or phosphonium cation $Q^+$ is preferably selected from the group formed by N-butylpyridinium, N-ethylpyridinium, pyridinium, 3-ethyl-1-methylimidazolium, 3-butyl-1-methylimidazolium, 3-hexyl-1-methylimidazolium, 3-butyl-1,2-dimethylimidazolium, diethylpyrazolium, N-butyl-N-methylpyrrolidinium, trimethylphenylammonium, tetrabutyl-phosphonium and tributyl-tetradecylphosphonium.

The sulfonium cations considered as cations $Q^+$ of the invention have general formula $SR^1R^2R^{3+}$, in which $R^1$, $R^2$ and $R^3$, which may be identical or different, each represent hydrocarbyl residues containing 1 to 12 carbon atoms, for example alkyl groups, saturated or unsaturated groups, cycloalkyl or aromatic, aryl, alkaryl or aralkyl groups, which may be substituted, containing 1 to 12 carbon atoms.

Examples of salts that can be used in the invention that can be cited are N-butylpyridinium hexafluorophosphate, N-ethylpyridinium tetrafluoroborate, pyridinium fluorosulfonate, 3-butyl-1-methylimidazolium tetrafluoroborate, 3-butyl-1-methylimidazolium bis-trifluoromethanesulfonyl amide, triethylsulfonium bis-trifluoromethanesulfonyl amide, 3-butyl-1-methylimidazolium hexafluoroantimonate, 3-butyl-1-methylimidazolium hexafluoro-phosphate, 3-butyl-1-methylimidazolium trifluoroacetate, 3-butyl-1-methylimidazolium trifluoromethylsulfonate, trimethylphenylammonium hexafluorophosphate and tetrabutyl-phosphonium tetrafluoroborate. Those salts can be used alone or as a mixture.

The acids used in accordance with the invention are defined as being organic compounds that can donate at least one proton. These acids have formula $H^+X^-$ in which $X^-$ represents an anion.

Anions $X^-$ are preferably selected from tetrafluoroborate, tetraalkylborates, hexafluorophosphate, hexafluoroantimonate, alkylsulfonates (for example methylsulfonate), perfluorosulfonates (for example trifluoromethylsulfonate), fluorosulfonate, sulfates, phosphates, perfluoroacetates (for example trifluoroacetate), perfluorosulfonamides (for example bis-trifluoromethanesulfonyl amide with formula $N(CF_3SO_2)_2^-$), fluorosulfonamides, perfluoro-sulfomethides (for example tris-trifluoromethanesulfonyl methylide with formula $C(CF_3SO_2)_3^-$), carborane anions, the tetraphenylborate anion as well as tetraphenylborate anions wherein the aromatic rings have been substituted.

The acids $H^+X^-$ used in the invention can be used alone or as a mixture.

The compounds used in the catalyst composition of the invention can be mixed in any order. Mixing can be achieved by simple contact followed by stirring until a homogeneous liquid is formed. Mixing can be carried out outside the dimerization or oligomerization reactor or, as is preferable, in the reactor.

In general, the catalyst composition can contain an organic solvent such as a hydrocarbon compound, for example an alkane or an aromatic hydrocarbon, or a chlorinated solvent.

The concentration of the nickel compound in the ionic liquid is advantageously in the range 0.01 mmole per liter of ionic liquid to 500 mmoles per liter, preferably in the range 0.05 to 100 mmoles per liter.

The invention also pertains to novel catalyst compositions for use for dimerization, co-dimerization, oligomerization or polymerization of olefins.

Catalytic systems comprising transition metals from groups 8–10, such as iron, nickel, palladium or cobalt, associated with diimine type ligands, have recently been developed and applied in polymerizing ethylene or co-polymerizing α-olefins or olefins carrying a function, such as methyl acrylate (see, for example, the review by V Gibson in Angew Chem Int Ed 1999, 38, 429). Those systems usually employ a co-catalyst which is an aluminum derivative such as an aluminoxane.

Further, neutral nickel complexes comprising chelate P—O type ligands have been used for more than twenty years as precursors in the "SHOP" process from Shell for oligomerizing ethylene to linear $C_4$–$C_{20+}$ α-olefins. The particular feature of that process is that the nickel complex is dissolved in a polar diol type solvent such as 1,4-butanediol, in which the reaction products are only slightly miscible. This use of a two-phase medium allows the products to be separated by decanting and allows the catalyst to be recycled.

We have now discovered a novel catalyst composition comprising at least one zero-valent nickel complex; at least one acid with formula $H^+X^-$ in which $X^-$ represents an anion; at least one nitrogen-containing ligand and at least one non-aqueous ionic liquid with general formula $Q^+A^-$ in which $Q^+$ represents a quaternary ammonium cation and/or a quaternary phosphonium cation and/or a sulfonium cation and in which $A^-$ is an anion identical to or different from $X^-$ and represents any anion that is capable of forming a liquid salt at low temperature, i.e., below This novel composition allows olefins to be dimerized, co-dimerized, oligomerized or polymerized. In particular, depending on the nature of the nitrogen-containing ligand employed, its steric and electronic hindrance, it is possible to orientate the reaction towards the formation of polymers, dimers or oligomers.

The nitrogen-containing ligand considered in the invention is preferably selected from the group formed by monoamines, di-, tri- and polyamines, imines, di-imines, pyridine and substituted pyridines, bi-pyridine, imidazole and substituted imidazoles, pyrrole and substituted pyrroles, pyrazole and substituted pyrazoles.

Particular examples of nitrogen-containing diimine type ligands have general formula:

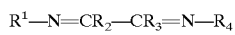

in which $R_1$ and $R_4$, which may be identical or different, each represent a hydrocarbyl group containing 1 to 12 carbon atoms, for example an alkyl group, a saturated or unsaturated group, a cycloalkyl or aromatic, aryl or aralkyl group, containing 1 to 12 carbon atoms, and $R_2$ and $R_3$, which may be identical or different, each represent hydrogen or a hydrocarbyl residue defined as $R_1$ and $R_4$.

The following developed formulae illustrate some of these products:

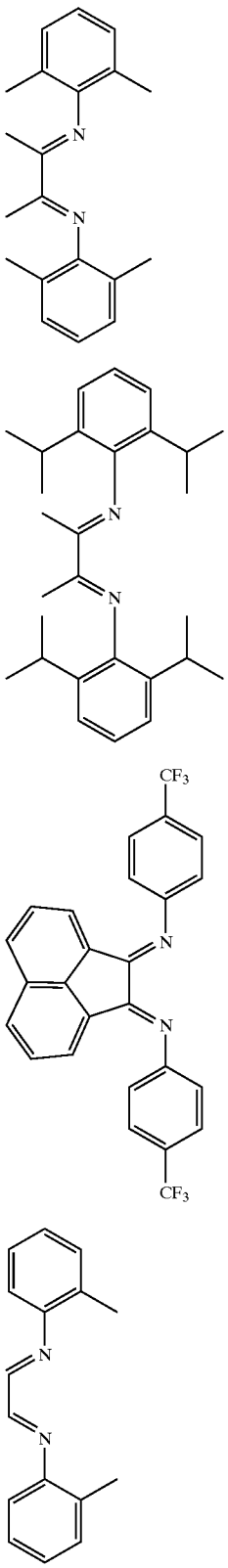

More particular olefins that can be dimerized, co-dimerized or oligomerized and in some circumstances polymerized by the catalyst compositions of the invention are ethylene, propylene, n-butenes and n-pentenes, used alone or as a mixture (co-dimerization), pure or diluted by an alkane, such as those found in cuts from oil refining processes such as catalytic cracking or steam cracking.

The catalytic olefin dimerization or oligomerization reaction or polymerization reaction can be carried out in a closed, semi-open or continuous system, with one or more-reaction stages. Vigorous stirring ensures good contact between the reactant or reactants and the catalyst mixture. The reaction temperature can be from −40° C. to +150° C., preferably −10° C. to +100° C. It is possible to operate above or below the medium melting temperature, the dispersed solid state not being a limitation on the reaction taking its proper course. The heat released by the reaction can be eliminated by any means that is known to the skilled person.

The pressure can be from atmospheric pressure to 70 MPa. The reaction products and the reactant or reactants which have not reacted are separated from the catalytic system by simple decanting, then fractionated.

EXAMPLES

The following examples illustrate the invention without limiting its scope. The following abbreviations are used n the examples:

BMI: 3-butyl-1-methylimidazolium;

NTf$_2$: N(CF$_3$SO$_2$)$_2^-$;

COD: cyclooctadiene.

Example 1

Oligomerization of Ethylene from a Nickel (0) Complex in the Presence of the Acid [H(Et$_2$O)$_2$]$^+$ [(3,5-(CF$_3$)$_2$C$_6$H$_3$)$_4$B]$^-$ in a BMI-NTf$_2$ Salt A Grignard reactor was vacuum dried (1 Pa) at 90° C. for 4 hours then cooled to ambient temperature under ethylene (2.8 MPa). After depressurizing, a solution of Ni(COD)$_2$ (sold by STREM), used without further purification (28 mg, 0.1 mmole), in 5 ml of distilled toluene was introduced using a syringe. The reactor was then closed, placed under ethylene (1.0 MPa) and the solution was stirred for 10 min at ambient temperature. After degassing to atmospheric pressure, a solution of the acid [H(Et$_2$O)$_2$]$^+$[(3,5-(CF$_3$)$_2$C$_6$H$_3$)$_4$B]$^-$ (Brookhart et al., Organometallics 1992, 11, 3920–3922) (101 mg, 0.1 mmole) in 5 ml of the molten salt BMI-NTf$_2$ was added to the nickel (0) solution using a syringe. The reactor was placed under ethylene (2.8 MPa) and the solution was stirred (750 rpm) for 1 hour at 25° C.

The gas phase was measured by a flow meter and recovered in a tank. The reactor was opened at −5° C. and the two-phase liquid mixture was rapidly distilled and weighed. The gas and liquid phases (distillation head) were analyzed using GC (PONA capillary column, injector at 250° C., temperature program: 35° C./10 min, 5° C./min, 70° C./10 min, 10° C./min, 270° C./10 min).

The weight of oligomers formed was 15.8 g (2687 g of oligomers per gram of nickel) distributed as follows: C$_4$: 60% (of which 33% of 1-butene), C$_6$: 35% (of which 8% of 1-hexene), C$_8$: 5% (no 1-octene detected).

Example 2

Oligomerization of Ethylene from a Nickel (0) Complex in the Presence of the Acid [H(Et$_2$O)$_2$]$^+$ [(3,5-(CF$_3$)$_2$C$_6$H$_3$)$_4$B]$^-$ in a BMI-SbF$_6$ Salt A Grignard reactor was vacuum dried (1 Pa) at 90° C. for 4 hours then cooled to ambient temperature under ethylene (2.8 MPa). After depressurizing, a solution of Ni(COD)$_2$ (6 mg, 0.02 mmole) in 5 ml of distilled toluene was introduced using a syringe. The reactor was then closed, placed under ethylene (1 MPa) and the solution was stirred for 10 min at ambient temperature. After degassing to atmospheric pressure, a solution of the acid [H(Et$_2$O)$_2$]$^+$[(3,5-(CF$_3$)$_2$C$_6$H$_3$)$_4$B]$^-$ (26 mg, 0.02 mmole) in 5 ml of the molten salt BMI-SbF$_6$ was added to the nickel (0) solution using a syringe. The reactor was placed under ethylene (2.8 MPa) and the solution was stirred (750 rpm) for 180 minutes.

The gas phase was measured by a flow meter and recovered in a tank. The reactor was opened at −5° C. and the two-phase liquid mixture was rapidly distilled and weighed. The gas and liquid phases (distillation head) were analyzed using GC (PONA capillary column, injector at 250° C., temperature program: 35° C./10 min, 5° C./min, 70° C./10 min, 10° C./min, 270° C./10 min).

The weight of oligomers formed was 28 g (23810 g of oligomers per gram of nickel) distributed as follows: C$_4$: 64% (of which 34% of 1-butene), C$_6$: 29% (of which 8% of 1-hexene), C$_8$: 6% (of which 3% 1-octene) and C$_{10}$: 1% (no 1-decene detected).

Example 3

Oligomerization of Ethylene from a Nickel (0) Complex in the Presence of the Acid HN(CF$_3$SO$_2$)$_2$ in a BMI-NTf$_2$ Salt A Grignard reactor was vacuum dried (1 Pa) at 90° C. for 4 hours then cooled to ambient temperature under ethylene (2.8 MPa). After depressurizing, a solution of Ni(COD)$_2$ (28 mg, 0.1 mmole) in 5 ml of distilled toluene was introduced using a syringe. The reactor was then closed, placed under ethylene (1.0 bars) and the solution was stirred for 10 min at ambient temperature. After degassing to atmospheric pressure, a solution of the acid HNTf$_2$ (28 mg, 0.1 mmole) in 5 ml of the molten salt BMI-NTf$_2$ was added to the nickel (0) solution using a syringe. The reactor was placed under ethylene (2.8 MPa) and the solution was stirred (750 rpm) for 1 hour at 25° C.

The gas phase was measured by a flow meter and recovered in a tank. The reactor was opened at −5° C. and the two-phase liquid mixture was rapidly distilled and weighed. The gas and liquid phases (distillation head) were analyzed using GC (PONA capillary column, injector at 250° C., temperature program: 35° C./10 min, 5° C./min, 70° C./10 min, 10° C./min, 270° C./10 min).

The weight of oligomers formed was 17 g (2891 g of oligomers per gram of nickel) distributed as follows: C$_4$: 60% (of which 32% of 1-butene), C$_6$: 36% (of which 7% of 1-hexene), C$_8$: 4% (of which 4% of 1-octene).

Example 4

Oligomerization of Ethylene from a Nickel (0) Complex in the Presence of the Acid [H(Et$_2$O)$_2$]$^+$ [(3,5-(CF$_3$)$_2$C$_6$H$_3$)$_4$B]$^-$ in a BMI-SbF$_6$ Salt The procedure of Example 2 was followed with the exception that Ni(COD)$_2$ (14 mg, 0.05 mmole) dissolved in 5 ml of toluene and the acid [H(Et$_2$O)$_2$]$^+$[(3,5-(CF$_3$)$_2$C$_6$H$_3$)$_4$B]$^-$ (55 mg, 0.05 mmole) dissolved in 5 ml of the molten salt BMI-SbF$_6$ were pre-mixed in a Schlenk tube under argon before being introduced into the pre-dried reactor that was in an ethylene atmosphere.

The reactor was placed under ethylene (2.8 MPa) and the solution was stirred (750 rpm) for 200 minutes at 25° C.

The gas phase was measured by a flow meter and recovered in a tank. The reactor was opened at −5° C. and the two-phase liquid mixture was rapidly distilled and weighed. The gas and liquid phases (distillation head) were analyzed using GC (PONA capillary column, injector at 250° C., temperature program: 35° C./10 min, 5° C./min, 70° C./10 min, 10° C./min, 270° C./10 min).

The weight of oligomers formed was 47 g (15986 g of oligomers per gram of nickel) distributed as follows: C$_4$: 61% (of which 27% of 1-butene), C$_6$: 30% (of which 4% of 1-hexene), C$_8$: 8% (of which 1% of 1-octene) and C$_{10}$: 1% (no 1-decene detected).

Example 5 (Comparative)

Oligomerization of Ethylene from a Nickel (0) Complex in the Presence of the Acid [H(Et$_2$O)$_2$]$^+$ [(3,5-(CF$_3$)$_2$C$_6$H$_3$)$_4$B]$^-$ in Toluene A Grignard reactor was vacuum dried (1 Pa) at 90° C. for 4 hours then cooled to ambient temperature under ethylene (2.8 MPa). After depressurizing, a solution of Ni(COD)$_2$ (55 mg, 0.2 mmole) in 10 ml of distilled toluene was introduced using a syringe. The reactor was then closed, placed under ethylene (1.0 MPa) and the solution was stirred for 10 min at ambient temperature. After degassing to atmospheric pressure, a solution of the acid [H(Et$_2$O)$_2$]$^+$[(3,5-(CF$_3$)$_2$C$_6$H$_3$)$_4$B]$^-$ (200 mg, 0.2 mmole) in 10 ml of toluene was added to the nickel (0) solution using a syringe. The reactor was placed under ethylene (2.8 MPa) and the solution was stirred (750 rpm) for 2 hours.

The gas phase was measured by a flow meter and recovered in a tank. The reactor was opened at −5° C. and the two-phase liquid mixture was rapidly distilled and weighed. The gas and liquid phases (distillation head) were analyzed using GC (PONA capillary column, injector at 250° C., temperature program: 35° C./10 min, 5° C./min, 70° C./10 min, 10° C./min, 270° C./10 min).

The weight of oligomers formed was 3.6 g (306 g of oligomers per gram of nickel) distributed as follows: C$_4$: 98% (of which 75% of 1-butene), C$_6$: 2% (of which 37% of 1-hexene).

Example 6

Oligomerization of 1-Butene from a Nickel (0) Complex in the Presence of the Acid [H(Et$_2$O)$_2$]$^+$ [(3,5-(CF$_3$)$_2$C$_6$H$_3$)$_4$B]$^-$ in a BMI-SbF$_6$ Salt A Grignard reactor was vacuum dried (1 Pa) at 90° C. for 4 hours then cooled to ambient temperature under argon (2.8 MPa). A solution of Ni(COD)$_2$ (14 mg, 0.05 mmole) in 5 ml of distilled toluene then 30 ml of 1-butene (mixture of 95% 1-butene and 5% of butane [internal reference]) was then added using a syringe. A solution of the acid [H(Et$_2$O)$_2$]$^+$ [(3,5-(CF$_3$)$_2$C$_6$H$_3$)$_4$B]$^-$ (50 mg, 0.05 mmole) in 5 ml of BMI-SbF$_6$ was injected using a syringe. The solution was stirred and the conversion was monitored by removing gas samples. After 320 minutes at 25° C., stirring was stopped, the reactor was degassed then cooled to −5° C. The liquid mixture was then distilled under constant vacuum and the distillation head was analyzed by GC (PONA capillary column, injector at 250° C., temperature program: 35° C./10 min, 5° C./min, 70° C./10 min, 10° C./min, 270° C./10 min).

The conversion was 49%. 88% of octenes and 12% of dodecenes were obtained.

Example 7

Oligomerization of Ethylene by a Ni(COD)$_2$ Complex in the Presence of the Ligand Acenaphthyl-bis(4-trifluoromethylphenylimine) and the Acid [H(Et$_2$O)$_2$]$^+$[(3,5-(CF$_3$)$_2$C$_6$H$_3$)$_4$B]$^-$ in BMI-NTf$_2$ A Grignard reactor was vacuum dried (1 Pa) at 90° C. for 4 hours then cooled to ambient temperature under ethylene (2.8 MPa). After depressurizing, a solution of Ni(COD)$_2$ (sold by STREM), used without further purification (28 mg, 0.1 mmole) in 5 ml of distilled toluene, was introduced using a syringe, along with a solution of the acid [H(Et$_2$O)$_2$]$^+$[(3,5-(CF$_3$)$_2$C$_6$H$_3$)$_4$B]$^-$ in 5 ml of BMI-NTf$_2$. The reactor was placed under ethylene (1.0 MPa) and the solution was stirred (750 rpm) for 5 minutes. After depressurizing, a solution of the ligand acenaphthyl-bis(4-trifluoromethylphenylimine) (47 mg, 0.1 mmole) was injected. The reactor was placed under ethylene (2.8 MPa) and the solution was stirred (750 rpm) for 80 minutes.

The gas phase was measured by a flow meter and recovered in a tank. The reactor was opened at –5° C. and the two-phase liquid mixture was rapidly distilled and weighed. The gas and liquid phases (distillation head) were analyzed using GC (PONA capillary column, injector at 250° C., temperature program: 35° C./10 min, 5° C./min, 70° C./10 min, 10° C./min, 270° C./10 min).

The weight of oligomers formed was 6.5 g (1100 g of oligomers per gram of nickel) distributed as follows: C$_4$: 57% (of which 43% of 1-butene), C$_6$: 15% (of which 50% of 1-hexene), C$_8$: 9% (of which 50% of 1-octene), C$_{10}$: 7% (of which 41% of 1-decene) and C$_{12}$+: 12%).

Example 8

Oligomerization of Ethylene by a Ni(COD)$_2$ Complex in the Presence of the Ligand Glyoxal-bis (4-methylphenylimine) and the Acid [H(Et$_2$O)$_2$]$^+$ [(3,5-(CF$_3$)$_2$C$_6$H$_3$)$_4$B]$^-$ in BMI-NTf$_2$ A Grignard reactor was vacuum dried (1 Pa) at 90° C. for 4 hours then cooled to ambient temperature under ethylene (2.8 MPa). After depressurizing, a solution of Ni(COD)$_2$ (28 mg, 0.1 mmole) in 5 ml of distilled toluene was introduced using a syringe, along with a solution of the acid [H(Et$_2$O)$_2$]$^+$[(3,5-(CF$_3$)$_2$C$_6$H$_3$)$_4$B]$^-$ (101 mg, 0.1 mmole) in 5 ml BMI-NTf$_2$. The reactor was placed under ethylene (1.0 MPa) and the solution was stirred (750 rpm) for 5 minutes. After depressurizing, a solution of the ligand glyoxal-bis(4-methylphenylimine) (24 mg, 0.1 mmole) was injected. The reactor was placed under ethylene (2.8 MPa) and the solution was stirred (750 rpm) for 80 minutes.

The gas phase was measured by a flow meter and recovered in a tank. The reactor was opened at –5° C. and the two-phase liquid mixture was rapidly distilled and weighed. The gas and liquid phases (distillation head) were analyzed using GC (PONA capillary column, injector at 250° C., temperature program: 35° C./10 min, 5° C./min, 70° C./10 min, 10° C./min, 270° C./20 min).

The weight of oligomers formed was 3 g (510 g of oligomers per gram of nickel) distributed as follows: C$_4$: 79% (of which 60% of 1-butene), C$_6$: 13% (of which 42% of 1-hexene), C$_8$: 5% (of which 28% of 1-octene), C$_{10}$: 2% and C$_{12}$+: 1%).

Example 9

Oligomerization of Ethylene by a Ni(COD)$_2$ Complex in the Presence of the Ligand Acenaphthyl-bis(4-trifluoromethylphenylimine) 3 and the Acid [H(Et$_2$O)$_2$]$^+$[(3,5-(CF$_3$)$_2$C$_6$H$_3$)$_4$B]$^-$ in BMI-SbF$_6$ A Grignard reactor was vacuum dried (1 Pa) at 90° C. for 4 hours then cooled to ambient temperature under ethylene (2.8 MPa). After depressurizing, a solution of Ni(COD)$_2$ (14 mg, 0.05 mmole) in 5 ml of distilled toluene was introduced using a syringe, along with a solution of the acid [H(Et$_2$O)$_2$]$^+$[(3,5-(CF$_3$)$_2$C$_6$H$_3$)$_4$B]$^-$ (50 mg, 0.05 mmole) in 5 ml BMI-SbF$_6$. The reactor was placed under ethylene (1.0 MPa) and the solution was stirred (750 rpm) for 5 minutes. After depressurizing, a solution of the ligand acenaphthyl-bis(4-trifluoromethylphenylimine) (24 mg, 0.05 mmole) was injected. The reactor was placed under ethylene (2.8 MPa) and the solution was stirred (750 rpm) for 80 minutes.

The gas phase was measured by a flow meter and recovered in a tank. The reactor was opened at –5° C. and the two-phase liquid mixture was rapidly distilled and weighed. The gas and liquid phases (distillation head) were analyzed using GC (PONA capillary column, injector at 250° C., temperature program: 35° C./10 min, 5° C./min, 70° C./10 min, 10° C./min, 270° C./20 min).

The weight of oligomers formed was 4 g (1360 g of oligomers per gram of nickel) distributed as follows: C$_4$: 29% (of which 62% of 1-butene), C$_6$: 23% (of which 61% of 1-hexene), C$_8$: 17% (of which 62% of 1-octene), C$_{10}$: 5% (of which 61% of 1-decene) and C$_{12}$+: 26%).

Example 10

Polymerization of Ethylene Starting from a Ni(0) Complex, the Ligand Diacetyl-bis(2,6-diisopropylphenylimine) and the Acid [H(Et$_2$O)$_2$]$^+$ [(3,5-(CF$_3$)$_2$C$_6$H$_3$)$_4$B]$^-$ in BMI-NTf$_2$ Diacetyl-bis(2,6-diisopropylphenylimine) (41 mg, 0.1 mmole) was reacted with one equivalent of the acid [H(Et$_2$O)$_2$]$^+$[(3,5-(CF$_3$)$_2$C$_6$H$_3$)$_4$B]$^-$ (101 mg, 0.1 mmole) in diethyl ether. After formation of the diimine-acid complex (see Published U.S. patent application Ser. No. 00/5,880, 323), the ether was evaporated off to obtain a red solid.

A Grignard reactor was vacuum dried (1 Pa) at 90° C. for 4 hours then cooled to ambient temperature under ethylene (2.8 MPa). After depressurizing, a solution of Ni (COD)$_2$ (28 mg, 0.1 mmole) in 5 ml of distilled toluene was introduced into the autoclave using a syringe. The solution was stirred for 10 minutes under ethylene (0.5 MPa) then the reactor was degassed. The diimine-acid complex (0.1 mmole) in 5 ml of the molten salt BMI-NTf$_2$ was injected. The autoclave was pressurized under ethylene (2.8 MPa) and the solution was stirred (750 rpm) for one hour.

The gas phase was measured by a flow meter and recovered in a tank. The reactor was opened and the recovered polymer was washed with methanol then vacuum dried. The gas phase was analyzed using GC (PONA capillary column, injector at 250° C., temperature program: 35° C./10 min, 5° C./min, 70° C./10 min, 10° C./min, 270° C./10 min).

The weight of products formed was 5 g (97% of polymer, 3% of butenes) (850 g of product/g Ni).

Example 11

Polymerization of Ethylene Starting from a Ni(0) Complex, the Ligand Diacetyl-bis(2,6-dimethylphenylimine) and the Acid [H(Et$_2$O)$_2$]$^+$[(3,5-(CF$_3$)$_2$C$_6$H$_3$)$_4$B]$^-$ Diacetyl-bis(2,6-dimethylphenylimine) (15 mg, 0.05 mmole) was reacted with two equivalents of the acid [H(Et$_2$O)$_2$]$^+$[(3,5-(CF$_3$)$_2$C$_6$H$_3$)$_4$B]$^-$ (101 mg, 0.1 mmole) in diethyl ether. After formation of the diimine-acid complex, the ether was evaporated off to obtain a red solid.

A Grignard reactor was vacuum dried (1 Pa) at 90° C. for 4 hours then cooled to ambient temperature under ethylene (2.8 MPa). After depressurizing, a solution of Ni(COD)$_2$ (28 mg, 0.1 mmole) in 5 ml of distilled toluene was introduced into the autoclave using a syringe. The solution was stirred for 10 minutes under ethylene (0.5 MPa) then the reactor was degassed. The diimine-acid complex (0.1 mmole) in 5 ml of the molten salt BMI-NTf$_2$ was injected. The autoclave was pressurized under ethylene (2.8 MPa) and the solution was stirred (750 rpm) for one hour.

The gas phase was measured by a flow meter and recovered in a tank. The reactor was opened and the recovered polymer was washed with methanol then vacuum dried. The gas phase was analyzed using GC (PONA capillary column, injector at 250° C., temperature program: 35° C./10 min, 5° C./min, 70° C./10 min, 10° C./min, 270° C./10 min).

The weight of products formed was 5 g (850 g of product per gram of nickel). It was distributed as follows: 80% of polymer and 20% of butenes (of which 55% of 1-butene).

Example 12

Polymerization of Ethylene Starting from a Ni(0) Complex, the Ligand Diacetyl-bis(2-methylphenylimine) and the Acid [H(Et$_2$O)$_2$]$^+$[(3,5-(CF$_3$)$_2$C$_6$H$_3$)$_4$B]$^-$ A Grignard reactor was vacuum dried (1 Pa) at 90° C. for 4 hours then cooled to ambient temperature under ethylene (2.8 MPa). After depressurizing, a solution of Ni(COD)$_2$ (28 mg, 0.1 mmole) in 5 ml of distilled toluene and a solution of the acid (101 mg, 0.1 mmole) in 5 ml of BMI-NTf$_2$ were introduced into the autoclave using a syringe. The solution was stirred for five minutes under ethylene (0.5 MPa) then the reactor was degassed. The ligand diacetyl-bis(2-methylphenylimine) (27 mg, 0.1 mmole) in 5 ml of distilled toluene was injected. The autoclave was pressurized under ethylene (2.8 MPa) and the solution was stirred (750 rpm) for one hour.

The gas phase was measured by a flow meter and recovered in a tank. The reactor was opened and the recovered polymer was washed with methanol then vacuum dried. The gas phase was analyzed using GC (PONA capillary column, injector at 250° C., temperature program: 35° C./10 min, 5° C./min, 70° C./10 min, 10° C./min, 270° C./10 min).

The weight of products formed was 14 g (2380 g of product per gram of nickel). It was distributed as follows: 97% of polymer and 3% of butanes (of which 55% of 1-butene).

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications cited above and below, and of corresponding French applications 02/01250 and 02/01252, filed Feb. 4, 2002, are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A catalyst composition in the form of a solution, consisting essentially of:
    at least one zero-valent nickel complex;
    at least one acid with formula H$^+$X$^-$ in which X$^-$ represents an anion;
    at least one ionic liquid with general formula Q$^+$A$^-$ in which Q$^+$ represents a quaternary ammonium cation and/or a quaternary phosphonium cation and/or a sulfonium cation and in which A$^-$ is an anion identical to or different from X$^-$ and is capable of forming a liquid salt with Q$^+$ at a temperature of less than 150° C., and
    at least one nitrogen-containing ligand bound to the zero valent nickel complex being in addition to those in the ionic liquid.

2. A catalyst according to claim 1, characterized in that said zero valent nickel complex is m nickel bis(cycloocta-1,3-diene), nickel bis(cyclooctatetraene), nickel bis(cycloocta-1,3,7-triene), bis(o-tolylphosphito) nickel (ethylene), nickel tetrakis (triphenylphosphite) or nickel bis(ethylene).

3. A catalyst composition according to claim 1, wherein in the formula H$^+$X$^-$, the anion X$^-$ is selected from the group consisting of: tetrafluoroborate, tetraalkylborates, hexafluorophosphate hexafluoroantimonate, alkylsulfonates, perfluorosulfonates, fluorosulfonate, sulfates, phosphates, perfluoroacetates, perfluorosulfonamides, fluorosulfonamides, perfluorosulfomethides, carborane anions, the tetraphenylborate anion and tetraphenylborate anions wherein the aromatic rings have been substituted.

4. A catalyst composition according to claim 1, wherein in the formula Q$^+$A$^-$, anion A$^-$ is selected from the group consisting of nitrate, sulfate, phosphate, acetate, halogenoacetate, tetrafluoroborate, tetrachloroborate, hexafluorophosphate, hexafluoroantimonate, fluorosulfonate alkylsulfonates, perfluoroalkylsulfonates, bis (perfluoroalkylsulfonyl) amides, tris-trifluoromethanesulfonyl methylide of formula C(CF$_3$SO$_2$)$_3$$^-$, arenesulfonates, arenesulfonates substituted with halogen or halogenalkyl groups, carborane anions, and the tetraphenylborate anion and tetraphenylborate anions the aromatic rings of which have been substituted.

5. A catalyst composition according to claim 1, wherein in the formula Q$^+$A$^-$, cations Q$^+$ are quaternary ammonium and/or phosphonium cations of formulae NR$^1$R$^2$R$^3$R$^{4+}$, PR$^1$R$^2$R$^3$R$^{4+}$, R$^1$R$^2$N=CR$^3$R$^{4+}$, or R$^1$R$^2$P=CR$^3$R$^{4+}$, in which R$^1$, R$^2$, R$^3$ and R$^4$, which are identical or different, are each a hydrogen atom with the exception of the cation NH$_4$$^+$ for NR$^1$R$^2$R$^3$R$^{4+}$, or a saturated or unsaturated aliphatic group, or a cycloalkyl or aromatic, aryl or aralkyl group, which are optionally substituted, containing 1 to 30 carbon atoms.

6. A catalyst composition according to claim 1, wherein in the formula Q$^+$A$^-$, cations Q$^+$ are quaternary ammonium and/or phosphonium cations derived from nitrogen-containing and/or phosphorus-containing heterocycles containing 1, 2 or 3 nitrogen and/or phosphorus atoms, said cations having the general formulae:

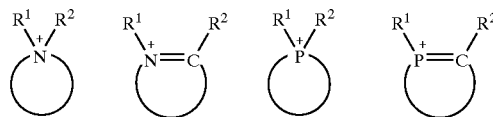

in which the cycles contain 4 to 10 ring atoms, and R$^1$ and R$^2$, which are identical or different, are each a hydrogen atom or a saturated or unsaturated aliphatic group, or a cycloalkyl or aromatic, aryl or aralkyl group which are optionally substituted, said cations containing 1 to 30 carbon atoms.

7. A catalyst composition according to claim 1, wherein in the formula $Q^+A^-$, cations $Q^+$ are quaternary ammonium and/or phosphonium cations of formulae:

$R^1R^{2+}N=C(R^3)—R^5—(R^3)C=N^+R^1R^2$ or $R^1R^{2+}P=C(R^3)—R^5—(R^3)C=P^+R^1R^2$, in which $R^1$, $R^2$ and $R^3$, which are identical or different, are each a hydrogen atom or a saturated or unsaturated aliphatic group, a cycloalkyl or aromatic, aryl or aralkyl group, which are optionally substituted, said cations containing 1 to 30 carbon atoms, and $R^5$ represents an alkylene or phenylene residue.

8. A catalyst composition according to claim 1, wherein in the formula $Q^+A^-$, cations $Q^+$ are quaternary ammonium and/or phosphonium cations selected from the group consisting of N-butylpyridinium, N-ethylpyridinium, pyridinium, 3-ethyl-1-methylimidazolium, 3-butyl-1-methylimidazolium, 3-hexyl-1-methylimidazolium, 3-butyl-1,2-dimethylimidazolium, diethylpyrazolium, N-butyl-N-methylpyrrolidinium, trimethylphenylammonium, tetrabutylphosphonium and tributyl-tetradecylphosphonium.

9. A catalyst composition according to claim 1, wherein in the formula $Q^+A^-$, cations $Q^+$ are sulfonium cations of the formula $SR^1R^2R^{3+}$, in which $R^1$, $R^2$ and $R^3$, which are identical or different, are each a saturated or unsaturated aliphatic group, or a cycloalkyl or aromatic, aryl, alkaryl or aralkyl group, each containing 1 to 12 carbon atoms.

10. A catalyst composition according to claim 1, wherein the ionic liquid is selected from the group consisting of N-butylpyridinium hexafluorophosphate, N-ethylpyridinium tetrafluoroborate, pyridinium fluorosulfonate, 3-butyl-1-methylimidazolium tetrafluoroborate, 3-butyl-1-methylimidazolium bis-trifluoromethanesulfonyl amide, triethylsulfonium bis-trifluoromethanesulfonyl amide, 3-butyl-1-methylimidazolium hexafluoroantimonate, 3-butyl-1-methylimidazolium hexafluorophosphate, 3-butyl-1-methylimidazolium trifluoroacetate, 3-butyl-1-methylimidazolium trifluoromethylsulfonate, trimethylphenylammonium hexafluorophosphate and tetrabutylphosphonium tetrafluoroborate.

11. A catalyst composition according to claim 1, wherein said composition contains an organic solvent selected from the group consisting of hydrocarbon compounds and chlorinated solvents.

12. A catalyst composition according to claim 1, wherein the concentration of nickel complex in the ionic liquid is in the range of 0.01 mmoles per liter of ionic liquid to 500 mmoles per liter.

13. A process comprising dimerizing, co-dimerizing or oligomerizing at least one olefin using a catalyst composition according to claim 1, wherein said olefin is ethylene, propylene, n-butenes and n-pentenes, used alone or as a mixture, pure or diluted with an alkane, or cuts from catalytic cracking or steam cracking processes.

14. A process according to claim 13, characterized in that the reaction is carried out in a closed system, a semi-open system or continuously, with one or more reaction stages, with vigorous stirring, at a temperature of −40° to +150° C. and at a pressure between atmospheric pressure and 70 MPa.

15. A process according to claim 14, characterized in that the reaction products and the unreacted reactant or reactants are separated from the catalyst composition by decanting then fractionating.

16. A catalyst composition in the form of a solution, consisting of
    at least one zero-valent nickel complex;
    at least one acid with formula $H^+X^-$ in which $X^-$ represents an anion;
    at least one ionic liquid with general formula $Q^+A^-$ in which $Q^+$ represents a quaternary ammonium cation and/or a quaternary phosphonium cation and/or a sulfonium cation and in which $A^-$ is an anion identical to or different from $X^-$ and is capable of forming a liquid salt with $Q^+$ at a temperature of less than 150° C.

17. A catalyst composition according to claim 1, characterized in that said nitrogen-containing ligand is selected from the group consisting of monoamines, di-, tri- and polyamines, imines, di-imines, pyridine and substituted pyridines, bi-pyridine, imidazole and substituted imidazoles, pyrrole and substituted pyrroles, and pyrazole and substituted pyrazoles.

18. A catalyst composition according to claim 17, wherein said nitrogen containing ligand comprises a nitrogen containing diimine ligand of the general formula:

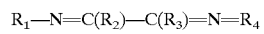

$R_1—N=C(R_2)—C(R_3)=N—R_4$ in which $R_1$ and $R_4$, which are identical or different, each represents a saturated or unsaturated aliphatic, or cycloalkyl or aromatic, aryl or aralkyl groups containing 1 to 12 carbon atoms, $R_2$ and $R_3$, which are identical or different, each represent hydrogen or a hydrocarbyl residue as defined for $R_1$ and $R_4$.

19. A catalyst composition according to claim 18, characterized in that said nitrogen-containing ligand has one of the following formulae:

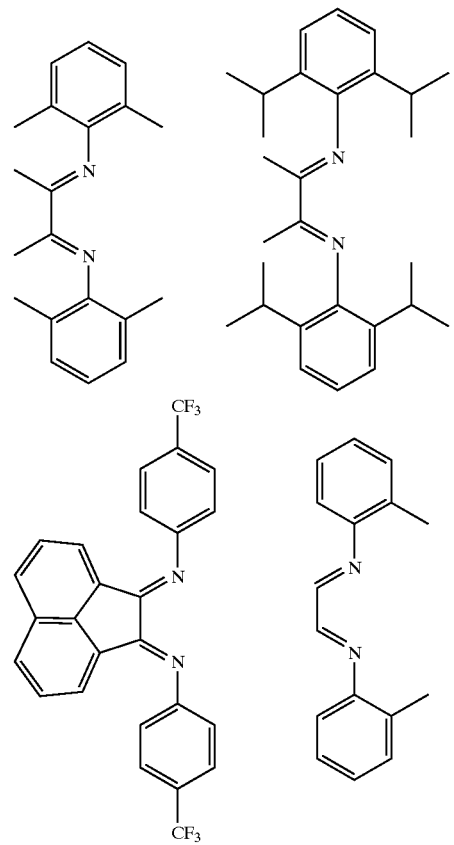

20. A catalyst composition in the form of a solution, consisting of
- at least one zero-valent nickel complex;
- at least one acid with formula $H^+X^-$ in which $X^-$ represents an anion;
- at least one ionic liquid with general formula $Q^+A^-$ in which $Q^+$ represents a quaternary ammonium cation and/or a quaternary phosphonium cation and/or a sulfonium cation and in which $A^-$ is an anion identical to or different from $X^-$ and is capable of forming a liquid salt with $Q^+$ at a temperature of less than 150° C.,
- at least one nitrogen-containing ligand bound to the zero valent nickel complex being in addition to those in the ionic liquid.

21. A catalyst composition according to claim 20, wherein in the formula $Q^+A^-$, anion $A^-$ is selected from the group consisting of nitrate, sulfate, phosphate, acetate, halogenoacetate, tetrafluoroborate, tetrachloroborate, hexafluorophosphate, hexafluoroantimonate, fluorosulfonate alkylsulfonates, perfluoroalkylsulfonates, bis(perfluoroalkylsulfonyl) amides, tris-trifluoromethanesulfonyl methylide of formula $C(CF_3SO_2)_3^-$, arenesulfonates, arenesulfonates substituted with halogen or halogenalkyl groups, carborane anions, the tetraphenylborate anion and tetraphenylborate anions the aromatic rings of which have been substituted.

22. A process comprising dimerizing, co-dimerizing, oligomerizing or polymerizing at least one olefin using a catalyst composition according to claim 20, wherein said olefin is ethylene, propylene, n-butenes and n-pentenes, used alone or as a mixture, pure or diluted by an alkane, or cuts from oil refining processes such as catalytic cracking or steam cracking.

23. A process according to claim 22, characterized in that the reaction is carried out in a closed, semi-open or continuous system, with one or more reaction stages, with vigorous stirring, at a temperature of −40° C. to +150° C. and at a pressure from atmospheric pressure to 70 MPa.

24. A process according to claim 23, characterized in that the reaction products and the unreacted reactant or reactants are separated from the catalyst composition by decanting then fractionating.

* * * * *